US008969419B2

(12) United States Patent
Garden et al.

(10) Patent No.: US 8,969,419 B2
(45) Date of Patent: Mar. 3, 2015

(54) ANIMAL FEED COMPOSITIONS AND FEEDING METHODS

(75) Inventors: Scott Garden, Yakima, WA (US); Lloyd Schantz, Washington, DC (US)

(73) Assignee: John I. Haas, Washington, DC (US)

( * ) Notice: Subject to any disclaimer, the term of this patent is extended or adjusted under 35 U.S.C. 154(b) by 34 days.

(21) Appl. No.: 13/265,731

(22) PCT Filed: Apr. 21, 2010

(86) PCT No.: PCT/US2010/001205
§ 371 (c)(1),
(2), (4) Date: Jan. 6, 2012

(87) PCT Pub. No.: WO2010/123571
PCT Pub. Date: Oct. 28, 2010

(65) Prior Publication Data
US 2012/0115960 A1    May 10, 2012

Related U.S. Application Data

(60) Provisional application No. 61/214,301, filed on Apr. 21, 2009.

(51) Int. Cl.
*A61K 31/12* (2006.01)
*A23K 1/17* (2006.01)
*A23K 1/18* (2006.01)
*A23K 1/14* (2006.01)
*A23K 1/16* (2006.01)
*C08B 37/16* (2006.01)
*C08L 5/16* (2006.01)

(52) U.S. Cl.
CPC .............. *A23K 1/1813* (2013.01); *A23K 1/14* (2013.01); *A23K 1/1612* (2013.01); *C08B 37/0015* (2013.01); *C08L 5/16* (2013.01)
USPC ............................ 514/689; 424/442; 424/750

(58) Field of Classification Search
USPC ........... 424/439, 442, 750; 514/678, 688, 689
See application file for complete search history.

(56) References Cited

U.S. PATENT DOCUMENTS

| 7,090,873 | B2 * | 8/2006 | Maye | 424/750 |
|---|---|---|---|---|
| 7,361,374 | B2 | 4/2008 | Wilson et al. | |
| 8,197,863 | B2 * | 6/2012 | Maye | 424/725 |
| 2004/0002423 | A1 | 1/2004 | Ohnogi et al. | |
| 2004/0137097 | A1 | 7/2004 | Maye | |
| 2006/0083775 | A1 | 4/2006 | Rigby et al. | |
| 2006/0269588 | A1 * | 11/2006 | Maye | 424/442 |
| 2008/0213342 | A1 * | 9/2008 | Maye | 424/442 |
| 2009/0042276 | A1 * | 2/2009 | Maye | 435/253.6 |
| 2011/0054024 | A1 * | 3/2011 | Maye | 514/553 |
| 2013/0018106 | A1 * | 1/2013 | Maye | 514/690 |

FOREIGN PATENT DOCUMENTS

| CN | 101011102 A | 8/2007 |
|---|---|---|
| JP | H01172331 A | 7/1989 |
| WO | WO-2004026041 A | 4/2004 |

OTHER PUBLICATIONS

Al-Mamun et al., "Responses of Plasma Acetate Metabolism to Hop (*Humulus lupulus* L.) in Sheep", Apr. 3, 2009, International Journal of Biological Sciences, 5(3), pp. 287-292.*
M.D. Flythe: "The antimicrobial effects of hops (*Humulus lupus* L.) on ruminal hyper ammonia-producing bacteria", Letters in Applied Microbiology, Mar. 1, 2009.
Feng, Yu-sheng et.al.; "Effect of Hop Residue Supplementation on Nutrient Metabolizing of Broilers", Hubei Agricultural Sciences, vol. 48, No. 7, Jul. 2009.
Chile Office Action corresponding to Chilean Application No. 2011-002623.
European Search Report corresponding to European Application No. 1067434.3.
New Zealand Examination Report for NZ Appln. No. 595585.
China Notification of Second Office Action for CN 201080026320.4.
Japanese Office Action for JP Appln. 2012-507218.
Australian Office Action for AU Appln. 2010239691.
Mohammad Al-Mamun et. al., "Responses of Plasma Acetate Metabolism to Hop (*Humulus lupulus* L.) in Sheep", Int. J. Biol. Sci, Apr. 3, 2009, vol. 5, No. 3, 287-292.
G. Krishna et. al., Fermentation of Various Preparation of Spent Hops (*Humulus lupulus* L.) Using the Rumen Simulation Technique (Rusitec), Agricultural Wastes, 1986, No. 17, 99-117.
Translation of and Mexican Office Action dated Jun. 4, 2014 for Mexican Patent Application No. MX/a/2011/011051.

* cited by examiner

*Primary Examiner* — My-Chau T Tran
(74) *Attorney, Agent, or Firm* — Locke Lord LLP; Jeffrey D. Hsi

(57) ABSTRACT

This invention relates to animal feed compositions. The invention also provides comprising a compound of this invention and the use of such compositions in methods of increasing and optimizing feed in animals.

14 Claims, No Drawings

ANIMAL FEED COMPOSITIONS AND FEEDING METHODS

CROSS-REFERENCE TO RELATED APPLICATIONS

This application is the national phase under 35 U.S.C. §371 of PCT International Application No.: PCT/US2010/001205, filed Apr. 21, 2010, which claims the benefit of U.S. provisional application 61/214,301, which was filed on Apr. 21, 2009. The entire contents of each of these applications are incorporated herein.

TECHNICAL FIELD OF THE INVENTION

This invention relates to animal feed compositions. The invention also provides compositions comprising a compound of this invention and the use of such compositions in methods of increasing and optimizing feed efficiency in animals.

BACKGROUND OF THE INVENTION

Livestock, such as cattle, chickens, and pigs, are fed some of the least expensive foodstuffs that farmers can purchase. Animals that graze and eat low quality feed may be subject to a diet contaminated with bacteria, protozoa, yeast, viruses and parasites. Animals rely on the integrity of their digestive tracts and ruminant animals in particular are dependent on the optimal function of their rumen microflora.

The rumen microflora is a complex system composed of a variety of microorganisms, and often of interest is the composition of bacteria and protozoa. Gram-negative bacteria are often considered to be beneficial to food and energy uptake, while certain Gram-positive bacteria and protozoa can reduce food and energy uptake and can be disruptive to rumen function.

High levels of microorganisms within the animal's digestive track can reduce food intake efficiency and cause the animal to become sick and even die. Inefficient utilization of feed also adversely effects the environment by increasing production of animal waste products containing high nitrogen levels and increasing animal methane emission. Ruminant animals are often targeted for digestive microflora control measures, but horses and other zoological animals also experience digestive disorders due to bacteria and protozoa infection.

Antibiotics in animal feed can kill bacteria and protozoa that have a negative impact animal growth. However, excessive use of antibiotics can negatively alter, or even destroy, digestive microflora causing the animal to become sick, and in some cases, die. Therefore, if antibiotics are to be used, they are often used at low levels to control the populations of harmful bacteria in the digestive tract.

Ionophores are a class of antibiotics commonly used in animal feed. Ionophores are molecules that transportions across biological membranes. Ionophores can have several oxygen atoms spaced throughout the molecule. The positions of the oxygen atoms create a cavity that can entrap cations. Ionophores have polar and non-polar regions that enhance cation entrapment and interaction with bacteria cell membranes. Ionophores are effective against Gram-positive bacteria and protozoa but generally innocuous to Gram-negative bacteria. By controlling the microorganism population and make-up in an animals digestive tract by inhibiting (or killing) select microorganisms, an animal's feed efficiency, as well as health and well being, can be improved.

Many people desire the ability to purchase and consume "natural" meat and poultry products. In Europe the sale, use, and importation of non-organic meat and poultry products is highly regulated. Meat and poultry products containing antibiotics would not be considered natural or organic products. With a growing market for natural or organic food there is a strong desire to discover alternatives to antibiotics. Also important from an agronomic and environmental standpoint are increased feed utilization, improved animal health, and reduced emissions of methane and ammonia. It is therefore desirable, from the perspective of both the consumer and producer, to create new and alternative approaches to common agricultural practices (such as antibiotic use) for increasing and optimizing animal performance. These and other limitations and problems of the past are solved by the present invention.

SUMMARY OF THE INVENTION

The invention relates to hop acid compounds, compositions comprising the compounds, and methods of using the compounds and compound compositions. The compounds and compositions comprising them are useful for increasing and optimizing feed efficiency in animals, including those mediated by or associated with digestive system microbiota in animals. The methods of using hop acids for increasing food and energy uptake from feed by livestock is described which includes delivering the hop acids for oral ingestion to the animals by mixing the acids with livestock feed. In particular, the invention is directed at replacing antibiotics (e.g., ionophore antibiotics, macrolide antibiotics) in animal feed with hop acids.

The present invention solves the problems set forth above by providing an hop acid compound. The hop plant, *Humulus lupulus*, produces organic acids known as alpha acids (humulone) and beta acids (lupulone). These hop acids include but are not limited to alpha acids and beta acids but also their isomerized forms, isomerized/reduced forms, hydrogenated forms, isomerized/hydrogenated forms, oxidized forms, as well as any salt forms. Beta acids include lupulone, colupulone, adlupulone, prelupulone as well as other analogs. Alpha acids include humulone, cohumulone, adhumulone, posthumulone, and prehumulone, as well as other analogs. They consist of a complex hexagonal molecule with several side chains, with ketone and alcohol groups. Each different humulone differs in the make-up of the side chain. Alpha acids are known to isomerize when exposed to heat to form isoalpha acids. Isoalpha acids and its reduced and/or hydrogenated forms, namely rho-isoalpha acids, tetrahydro-isoalpha acids and hexahydro-isoalpha acids are hop acids commonly used to flavor beer.

The compounds of this invention, and compositions comprising them, are useful for increasing and optimizing feed efficiency in animals by administration of the compounds or compositions comprising the compounds to the subject animals. It is determined that efficiency is improved by careful maintenance of pH levels in the digestive system of the animal (e.g., rumen in ruminants) in a prescribed range. In one aspect, the feed composition does not comprise an added nitrogen source component. In one aspect, the added nitrogen source component could be urea.

In one aspect is a method for feeding animals comprising administering to an animal a composition having an effective amount of hop acid wherein the pH of digestive fluid in the animal from the time immediately post feeding to 24 hours post-feeding is maintained in a range from about 5 to 8 (e.g., pH 5-7; pH 5-6).

In another aspect is a method for feeding animals comprising administering to an animal a composition having an effective amount of hop acid wherein the pH of a digestive fluid sample taken from the time immediately post feeding to 24 hours post-feeding is in a range from about 5 to 7 (e.g., pH 5-7; pH 5-6). In certain embodiments, the pH ranges from about 5 to 6. In other embodiments, the pH ranges from about 5.2 to about 7.

In certain embodiments, the hop acid is hop beta acid.

In other embodiments, the amount of hop acid administered to the animal is between 0.1-1000 mg/day. In certain embodiments, the amount of hop acid administered to the animal is between 1-300 mg/day.

In various embodiments, the animal is a ruminant animal. In certain embodiments, the animal is a bovine, an equine, a ruminant, a mammal, a food production animal, or the like.

Another aspect is a method for feeding animals comprising administering to an animal a composition having an effective amount of hop acid, wherein the concentration in digestive (e.g., rumen) fluid in the animal from the time immediately upon initiation of feeding to 24 hours post-feeding of the following is one or more of the following:

acetate is maintained in a range from about 30 to 50 mM;
propionate is maintained in a range from about 20 to 45 mM;
butyrate is maintained in a range from about 6 to 13 mM;
isobutyrate is maintained in a range from about 0.5 to 1.1 mM;
valerate is maintained in a range from about 2 to 4 mM;
isovalerate is maintained in a range from about 1.5 to 2.5 mM;
acetate:propionate concentration ratio is maintained in a range from about 0.75:2.95;
total volatile fatty acid (VFA) is maintained in a range from about 70 to 110 mM;
ammonia is maintained in a range from about 2 to 8 mM; and
lactate concentration is maintained in a range from about 0 to 2 mM.

Another aspect is a method for feeding animals comprising administering to an animal a composition having an effective amount of hop acid, wherein the concentration in digestive (e.g., rumen) fluid in the animal from the time immediately upon initiation of feeding to 20 hours post-feeding of the following is one or more of the following:

acetate is maintained in a range from about 30 to 50 mM;
propionate is maintained in a range from about 20 to 45 mM;
butyrate is maintained in a range from about 6 to 13 mM;
isobutyrate is maintained in a range from about 0.5 to 1.1 mM;
valerate is maintained in a range from about 2 to 4 mM;
isovalerate is maintained in a range from about 1.5 to 2.5 mM;
acetate:propionate concentration ratio is maintained in a range from about 1.25:2.00;
total volatile fatty acid (VFA) is maintained in a range from about 70 to 110 mM;
ammonia is maintained in a range from about 2 to 8 mM; and
lactate concentration is maintained in a range from about 0 to 2 mM.

In certain embodiments, the invention provides a method wherein the feed composition does not comprise an added nitrogen source component.

In other embodiments, the invention provides a method wherein the feed comprises a nitrogen source component. In certain embodiments, the component is urea.

In various embodiments, the invention provides a method wherein the animal is monitored. In a further embodiment, an animal is monitored for rumen fluid concentration levels for one or more of: acetate; propionate; butyrate isobutyrate; valerate; isovalerate; acetate:propionate concentration total volatile fatty acid (VFA); ammonia; or lactate. In certain embodiments, the invention provides a method wherein an animal is monitored for emission levels of methane, hydrogen sulfide or ammonia. Such monitoring is pursuant to compliance with a regulatory agency standard.

A method of using hop acids as a natural addition to feed for livestock is described including delivering the hop acids for oral ingestion by mixing the acids with livestock feed. The acids are mixed with the feed in an amount to regulate levels of animal digestive bacteria and bacteria by-products (e.g., hydrocarbon end products) in the livestock's digestive system. The composition and method described allows for the production of polyether ionophoric compound free livestock. In other aspects the amount of hop acid administered to the animal is between 0.1-100 mg/day; 0.1-200 mg/day; 1-300 mg/day; 50-200 mg/day; 80-160 mg/day; 125-175 mg/day (inclusive). In other aspects the amount of hop acid administered to the animal is any range between (inclusive) a lower limit of a number between 0.1-900 mg/day and an upper limit of a number between 1-1000 mg/day.

In another aspect, the invention relates to a method of increasing and optimizing feed efficiency in a subject in need thereof including administering to the subject an effective amount of a compound herein, or acceptable salt, solvate or hydrate thereof (or composition thereof). The feed efficiency can be modulated by any animal digestive system microbiota, including those specifically delineated herein. The animal digestive system microbiota can be those that degrade plant fiber or other feed materials (e.g., alfalfa, barley, corn, grass, oats, rye, soy, straw, wheat, etc.). The animal digestive system microbiota can be methanogens, those that live in syntropic relations with other digestive bacteria and protozoa that produce hydrogen and carbon dioxide end products.

The compositions and methods herein provide numerous benefits including providing improved and increased animal feeding efficiency; reduction of additional nitrogen source materials in the feed; improved uptake/usage of nitrogen; reduced ammonia waste generation by the animals; reduced methane generation by the animals; reduction in waste/waste disposal costs in animal production; improved environmental compliance in raising the animals; and generally regarded as safe (GRAS) compliant feeds/feed methods.

DETAILED DESCRIPTION OF THE INVENTION

Definitions

The term "hop acid" includes organic acids known as alpha acids (humulone) and beta acids (lupulone). These hop acids include but are not limited to alpha acids and beta acids but also their isomerized forms, isomerized/reduced forms, hydrogenated forms, isomerized/hydrogenated forms, oxidized forms, as well as any salt forms, including salt forms in aqueous solutions.

Beta acids include lupulone, colupulone, adlupulone, prelupulone as well as other analogs.

Alpha acids include humulone, cohumulone, adhumulone, posthumulone, and prehumulone, as well as other analogs.

Hop acids and hop acid salts used in the invention include commercially available products including, but not limited to, ALPHAHOP™, BETASTAB™, ISOHOP™, HEXAHOP GOLD™, REDIHOP™, TETRAHOP™, AND TETRAHOP GOLD™. Such compositions include an aqueous alkaline solution of a potassium salt of the corresponding hop acid. The compositions are known to those of ordinary skill in the art.

The terms "monensin" and "rumensin" here are used interchangeably and refer to a compound that belongs to a family of polyether ionophore antibiotics. The chemical name is 4-[2-[5-ethyl-5-[5-[6-hydroxy-6-(hydroxymethyl)-3,5-dimethyl-oxan-2-yl]-3-methyl-oxolan-2-yl]oxolan-2-yl]-9-hydroxy-2,8-dimethyl-1,6-dioxaspiro[4.5]dec-7-yl]-3-methoxy-2-methyl-pentanoic acid.

The term "ruminant animal" refers to a mammal of the order Artiodactyla that digests plant-based food by initially softening it within the animal's first stomach, then regurgitating the semi-digested mass, now known as cud, and chewing it again. The process of rechewing the cud to further break down plant matter and stimulate digestion is called "ruminating". Ruminating mammals include but are not limited to cattle, goats, sheep, giraffes, bison, yaks, water buffalo, deer, camels, alpacas, llamas, wildebeest, antelope, pronghorn, and nilgai.

The term "rumen" forms the larger part of the reticulorumen, which is the first chamber in the alimentary canal of ruminant animals. It serves as the primary site for microbial fermentation of ingested feed.

The term "rumen health" refers to a balance of microflora or bacteria in the rumen that is used to extract nutrients from feed. Various animal feeds are high in starch and/or carbohydrates, causing a decrease in rumen health resulting from microorganism growth, (e.g., *Lactobacillus* growth) and subsequent increase in lactate/lactic acid production.

The term "bovine" herein refers to the biological subfamily Bovinae, and includes a diverse group of 10 genera of medium to large sized ungulates, including domestic cattle, the bison, African buffalo, the water buffalo, the yak, and the four-horned and spiral-horned antelopes. General characteristics include cloven hoofs and usually at least one of the sexes of a species having true horns.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "compound" as used herein, is also intended to include salts, prodrugs, and prodrug salts of a compound herein. The term also includes any solvates, hydrates, and polymorphs of any of the foregoing. The specific recitation of "prodrug," "prodrug salt," "solvate," "hydrate," or "polymorph" in certain aspects of the invention described in this application shall not be interpreted as an intended omission of these forms in other aspects of the invention where the term "compound" is used without recitation of these other forms.

A salt of a compound of this invention is formed between an acid and a basic group of the compound, such as an amino functional group, or a base and an acidic group of the compound, such as a carboxyl functional group. According to another preferred embodiment, the compound is an animal feed acceptable acid addition salt.

As used herein and unless otherwise indicated, the term "derivative" means a structurally related compound that can hydrolyze, oxidize, or otherwise react under biological conditions (in vitro or in vivo) to provide a compound of this invention. Derivatives may only become active upon such reaction under biological conditions, or they may have activity in their unreacted forms. Examples of derivatives contemplated in this invention include, but are not limited to, analogs of compounds disclosed herein that comprise biohydrolyzable moieties such as amides, esters, carbamates, carbonates, and phosphate analogues.

As used herein and unless otherwise indicated, the term "biohydrolyzable moiety" means a functional group (e.g., amide, ester, carbamate, carbonate, or phosphate analogue, that either: 1) does not destroy the biological activity of the compound and confers upon that compound advantageous properties in vivo, such as uptake, duration of action, or onset of action; or 2) is itself biologically inactive but is converted in vivo to a biologically active compound.

A derivative salt is a compound formed between an acid and a basic group of the derivative, such as an amino functional group, or a base and an acidic group of the derivative, such as a carboxyl functional group. In a one embodiment, the derivative salt is a animal feed acceptable salt.

An "animal feed acceptable salt" means any non-toxic salt that, upon administration to a recipient, is capable of providing, either directly or indirectly, a compound or a derivative of a compound of this invention.

Acids commonly employed to form acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such animal feed acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred animal feed acceptable acid addition salts include those formed with mineral acids such as hydrochloric acid and hydrobromic acid, and especially those formed with organic acids such as maleic acid.

Suitable bases for forming animal feed acceptable salts with acidic functional groups of prodrugs of this invention include, but are not limited to, hydroxides of alkali metals such as sodium, potassium, and lithium; hydroxides of alkaline earth metal such as calcium and magnesium; hydroxides of other metals, such as aluminum and zinc; metals such as iron, copper, or any metal that can form a monovalent or divalent cationic species; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

As used herein, the term "polymorph" means solid crystalline forms of a compound or complex thereof which may be characterized by physical means such as, for instance, X-ray powder diffraction patterns or infrared spectroscopy. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "stable compounds", as used herein, refers to compounds which possess stability sufficient to allow manufacture and which maintain the integrity of the compound for a sufficient period of time to be useful for the purposes detailed herein (e.g., formulation into feed products, intermediates for use in production of feed compounds, isolatable or storable intermediate compounds).

"Stereoisomer" refers to both enantiomers and diastereomers.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

The compounds delineated herein are readily available from commercial sources, or can be readily effected by synthetic chemists of ordinary skill. Additional methods of synthesizing compounds herein and their synthetic precursors are within the means of chemists of ordinary skill in the art. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Combinations of substituents and variables envisioned by this invention are only those that result in the formation of stable compounds.

The invention also provides compositions comprising an effective amount of a compound herein (e.g., alpha hop acid or beta hop acid, or salts thereof), or an animal feed acceptable salt, solvate, hydrate, polymorph or prodrug, if applicable, of said compound; and an acceptable carrier. Preferably, a composition of this invention is formulated for animal feed use ("a feed composition"), wherein the carrier is a animal feed acceptable carrier. The carrier(s) must be "acceptable" in the sense of being compatible with the other ingredients of the formulation and, in the case of a animal feed acceptable carrier, not deleterious to the recipient thereof in amounts typically used in medicaments.

Animal feed acceptable carriers, adjuvants and vehicles that may be used in the animal feed compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, propylene glycol and wool fat. Other food materials or food grade materials useful in the hop acid compositions herein include molasses, honey, and other coating materials.

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

In another embodiment, a composition of the present invention further comprises a second animal feed agent. The second therapeutic agent includes any compound or feed agent known to have or that demonstrates advantageous properties when administered with the hop acid compounds herein. Preferably, the second therapeutic agent is an agent useful in the treatment or prevention of a disease or condition selected in the subject, including for example therapeutic agents, nutritional agents, feed efficiency agents.

In the animal feed compositions of the invention, the compound of the present invention is present in an effective amount. As used herein, the term "effective amount" refers to an amount which, when administered in a proper dosing regimen, is sufficient to exhibit a feed efficiency effect.

Methods of Treatment

In one aspect, the invention provides a method for enhancing the desired performance of a ruminant animal through the oral administration of a rumen pH modulating amount of a hop acid;
wherein the ruminant animal is administered an animal feed that is free from a polyether ionophore compound or macrolide antibiotic.

In a second aspect, the invention provides a method for improving survival of a group of ruminant animals through the oral administration of a rumen pH modulating amount of a hop acid;
wherein the survival is relative to a group of ruminant animals that is fed an animal feed that is free of a rumen pH modulating amount of a hop acid.

The invention also provides a method for improving rumen health and functionality of a group of ruminant animals through the oral administration of a rumen pH modulating amount of a hop acid;
wherein the rumen health and functionality are relative to a group of ruminant animals that is fed an animal feed that is free of a rumen pH modulating amount of a hop acid.

In a third aspect, the invention provides a method for enhancing the desired performance of a ruminant animal that had been administered a polyether ionophore or macrolide antibiotic containing an animal feed, comprising the step of discontinuing administration of a polyether ionophore or macrolide antibiotic feed, and administering a hop acid containing animal feed.

In certain embodiments, the oral administration of hop acids in a ruminant's diet includes a feed composition, feed supplement, feed ration, water ration, mineral lick, and/or bolus.

In various embodiments, the hop acid is derived from a hop or hop source, or is produced synthetically.

In one embodiment, the hop acid is a hop β-acid, or a salt thereof. In a further embodiment, the hop β-acid is lupulone, colupulone, adlupulone, hexahydro-lupulone, hexahydro-colupulone, hexahydro-adlupulone, or hulupone, or salts thereof.

In other embodiments, the hop acid is a hop α-acid, or a salt thereof. In a further embodiment, the hop α-acid is humulone, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, or hexahydro-isoadhumulone, or salts thereof.

In various embodiments, the amount of hop acid administered to the ruminant animal is between 0.1-1000 mg/animal/day. In a further embodiment, the hop acid is administered in an effective amount, including but not limited to, as part of a formulation, compounded mixture, salt, hydrate, solvate, and/or polymorph.

In one embodiment, the desired performance of a ruminant animal is an enhanced feed efficiency. In a further embodiment, the enhanced feed efficiency results in enhanced weight gain or enhanced milk production.

In another embodiment, the desired performance of a ruminant animal is decreased methane production.

In certain embodiments, the desired performance of a ruminant animal is increased rumen ammonia production. In other embodiments, the desired performance is enhanced by in increase in rumen ammonia production. In a further embodiment, the desired performance of a ruminant animal is enhanced by an increase in ammonia concentration, and the ammonia concentration of a rumen fluid or intestinal digesta sample at any time immediately upon initiation of feeding to 24 hours post-feeding is in the range from about 2 to 8 mM.

In still another embodiment, the pH of a rumen fluid or intestinal digesta sample from the time immediately upon initiation of feeding to 24 hours post-feeding is maintained in a range from about 5 to 8. In a further embodiment, the pH of rumen fluid or intestinal digesta sample from the time immediately upon initiation of feeding to 24 hours post-feeding is maintained in the preferable range from about 5.2 to 7.

In certain embodiments, the desired effect is to increase the pH of the rumen fluid or intestinal digesta by about 1% to about 25%; in certain embodiments about 1% to about 10%; in certain embodiments about 1% to about 5% using the method of the invention, compared to the pH measured from the rumen fluid or intestinal digesta of a ruminant animal feed an animal feed comprising a polyether ionophore compound, e.g., monensin. In certain embodiments, the increase in pH ranges from about 1% to about 3%. In other embodiments, the increase in pH ranges from about 2% to about 4%. In other embodiments, the increase in pH ranges from about 3% to about 5%. In other embodiments, the increase in pH ranges from about 5% to about 10%. In other embodiments, the increase in pH ranges from about 10% to about 15%. In other embodiments, the increase in pH ranges from about 15% to about 25%.

In certain embodiments, the desired performance of a ruminant animal is enhanced by an increase in total volatile fatty acid content in the rumen fluid or intestinal digesta. In other embodiments, the desired performance is an increase in total volatile fatty acid content in the rumen fluid or intestinal digesta. In a further embodiment, the total volatile fatty acid concentration in rumen fluid or intestinal digesta sample at any time immediately upon initiation of feeding to 24 hours post-feeding is in the range from about 70 to 110 mM.

In other embodiments, the desired performance of a ruminant animal is enhanced by an increase in acetate concentration in the rumen fluid or intestinal digesta. In other embodiments, the desired performance is an increase in acetate concentration in the rumen fluid or intestinal digesta. In a further embodiment, the concentration of acetate in rumen fluid or intestinal digesta sample at any time immediately upon initiation of feeding to 24 hours post-feeding is in the range from about 30 to 50 mM.

In other embodiments, the desired performance of a ruminant animal is increased rumen propionate production. In other embodiments, the desired performance of a ruminant animal is enhanced by increased rumen propionate production. In a further embodiment, the concentration of propionate in rumen fluid or intestinal digesta sample at any time immediately upon initiation of feeding to 24 hours post-feeding is in the range from about 20 to 45 mM.

In certain embodiments, the desired performance of a ruminant animal is enhanced by an increase in acetate to propionate concentration. In other embodiments, the desired performance of a ruminant animal is an increase in acetate to propionate concentration. In a further embodiment, the acetate to propionate concentration ratio in rumen fluid or intestinal digesta sample at any time immediately upon initiation of feeding to 24 hours post-feeding is maintained in a range from about 0.75 to 2.95.

In various embodiments, the desired performance of a ruminant animal is enhanced by a decrease in butyrate concentration. In other embodiments, the desired performance of a ruminant animal is a decrease in butyrate concentration. In a further embodiment, the concentration of butyrate in rumen fluid or intestinal digesta sample at any time immediately upon initiation of feeding to 24 hours post-feeding is in the range from about 6 to 13 mM.

In other embodiments, the desired performance of a ruminant animal is enhanced by an increase in isobutyrate concentration. In other embodiments, the desired performance of a ruminant animal is an increase in isobutyrate concentration. In a further embodiment, the concentration of isobutyrate in rumen fluid or intestinal digesta sample at any time immediately upon initiation of feeding to 24 hours post-feeding is in the range from about 0.5 to 1.1 mM.

In other embodiments, the desired performance of a ruminant animal is enhanced by an increase in valerate concentration. In other embodiments, the desired performance of a ruminant animal is an increase in valerate concentration. In a further embodiment, the concentration of valerate in rumen fluid or intestinal digesta sample at any time immediately upon initiation of feeding to 24 hours post-feeding is in the range from about 2 to 4 mM.

In certain embodiments, the desired performance of a ruminant animal is enhanced by an increase in isovalerate concentration. In other embodiments, the desired performance of a ruminant animal is an increase in isovalerate concentration. In a further embodiment, the isovalerate concentration in rumen fluid or intestinal digesta sample at any time immediately upon initiation of feeding to 24 hours post-feeding is in the range from about 1.5 to 2.5 mM.

In certain embodiments, the desired performance of a ruminant animal is a maintenance of lactate concentration. In other embodiments, the desired performance is enhanced by a maintenance of lactate concentration. In still other embodiments, the lactate concentration in rumen fluid or intestinal digesta sample is maintained in a range to minimize effects of dysfunctional ruminal metabolism. In a further embodiment, the lactate concentration in rumen fluid or intestinal digesta sample is within a desired range to prevent acidosis, subclinical acidosis and/or bloat. In still another further embodiment, the lactate concentration in rumen fluid or intestinal digesta sample at any time immediately upon initiation of feeding to 24 hours post-feeding is in the range from about 0 to 2 mM.

In other embodiments, the lactate concentration is reduced in rumen fluid or intestinal digesta sample to a range to minimize effects of dysfunctional ruminal metabolism.

In various embodiments, the animal feed does not comprise a polyether ionophore compound or macrolide antibiotic. In one embodiment, the polyether ionophore compound is monensin.

In other embodiments, the animal or group of animals does not suffer from acidosis.

In other embodiments, the pH of an animal rumen is higher than the pH of an animal rumen that is administered an animal feed treated with a polyether ionophore compound in the absence of hop acids. What is surprising and unexpected about the method of the invention is the maintenance of pH upon administration of an animal feed comprising a hop acid or salt thereof. Typically, the rumen pH of a ruminant animal that is fed a monensin treated animal feed decreases to the point of causing acidosis in the animal.

In another embodiment, the concentration in rumen fluid or intestinal digesta sample from the time immediately upon initiation of feeding to 24 hours post-feeding of the following is:

acetate is maintained in a range from about 30 to 50 mM;
propionate is maintained in a range from about 20 to 45 mM;
butyrate is maintained in a range from about 6 to 13 mM;
isobutyrate is maintained in a range from about 0.5 to 1.1 mM;
valerate is maintained in a range from about 2 to 4 mM;
isovalerate is maintained in a range from about 1.5 to 2.5 mM;
acetate:propionate concentration ratio is maintained in a range from about 0.75:2.95;
total volatile fatty acid (VFA) is maintained in a range from about 70 to 110 mM;
ammonia is maintained in a range from about 2 to 8 mM; and
lactate concentration is maintained in a range from about 0 to 2 mM.

In certain embodiments, the feed composition does not comprise an added nitrogen source.

In other embodiments, the feed composition further comprises a nitrogen source component. In certain embodiments, the nitrogen source component is urea, distillers grains, or other suitable nitrogen source, known to those of ordinary skill in the art.

In certain embodiments, improving survival of a group of ruminant animals includes improving the health of various animals, e.g., lowering mortality rates, decreasing the number of sick/unhealthy animals, etc.

According to another embodiment, the invention provides a method of increasing and optimizing feed efficiency in a subject comprising the step of administering to said subject an effective amount of a compound or a composition of this invention. Such diseases are well known in the art and are also disclosed herein.

According to another embodiment, the invention provides a method of increasing and optimizing feed efficiency in a subject comprising the step of administering to said subject an effective amount of animal feed made by combining any animal feed material (e.g., plant matter, grasses, grains, cereals, including those delineated herein) with hop acids delineated herein.

Methods delineated herein include those wherein the subject is identified as in need of a particular stated treatment. Identifying a subject in need of such treatment can be in the judgment of an animal care professional and can be subjective (e.g. opinion) or objective (e.g. measurable by a test or diagnostic method).

Methods delineated herein include those wherein a subject (an animal, a sample animal from a group or herd) is monitored. The monitoring can be performed to track progress of the feeding method or can track other measurements, including for example, measurement of emissions from an animal (e.g., methane production, ammonia production, hydrogen sulfide, environmental emission) subject to standards established by a regulatory agency (e.g., appropriate federal, state or local agency whether environmental, agricultural, food or other agency with regulatory jurisdiction); pH, chemical compound(s) concentration or ratios (e.g., including those delineated herein), chemical, bacterial, microbial, protein, nucleic acid other physicochemical or functional characteristic, or other marker. The monitoring can involve taking of one or more samples periodically through the feeding process, or from the animal after the feeding and digestion process is commenced or completed.

In another embodiment, the above method of treatment comprises the further step of co-administering to an animal one or more second therapeutic agents. The choice of second therapeutic agent may be made from any second therapeutic agent known to be useful for indications herein.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention comprising both a compound of the invention and a second therapeutic agent to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications. However, it is well within the skilled artisan's purview to determine the second therapeutic agent's optimal effective-amount range.

In yet another aspect, the invention provides the use of a compound herein (e.g., hop acids) alone or together with one or more of the above-described second therapeutic agents in the manufacture of a feed composition or feed medicament, either as a single composition or as separate dosage forms, for treatment or prevention in a subject of a disease, disorder, symptom, or for improving feeding efficiency or animal growth, or other use set forth herein. Another aspect of the invention is a compound herein for use in the treatment or prevention in a subject of a disease, disorder symptom, or for improving feeding efficiency or animal growth, or other use set forth herein.

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment. In one aspect, the feeding method is adjusted based on monitoring information collected as described herein to regulate or achieve metrics or marker levels herein.

The present invention also provides kits for use to treat a subject in need of an animal feed composition, including those where improved feed efficiency is desired. These kits comprise: a) an animal feed composition comprising a hop acid compound of herein or a salt thereof; or a prodrug, or a salt of a prodrug thereof; or a hydrate, solvate, or polymorph thereof, wherein said animal feed composition is in a container; and b) instructions describing a method of using the animal feed composition to improve feed efficiency (i.e., relative to feed efficiency achieved by administration of feed without the compositions of the invention delineated herein).

The container may be any vessel or other sealed or sealable apparatus that can hold said animal feed composition. Examples include bottles, divided or multi-chambered holders or bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of an animal feed acceptable material, for example a paper or cardboard box, a glass or plastic bottle or jar, a re-sealable bag (for example, to hold a "refill" of tablets for placement into a different container), or a container with individual doses for pressing out of the container. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box.

The major gas excreted by farm animals is carbon dioxide ($CO_2$), which is a fully oxidized carbon source. Methane ($CH_4$) an unoxidized carbon source is considered lost energy to the farm animal and is an environmental pollutant. It is estimated that about 2-12% of farm animal energy is lost due to methane gas excretion. As a result of this lost energy, the cost for feeding animals is increased. It is believed that farm animals are responsible for about 15-20% of the methane found in the atmosphere. This increase in methane is responsible in part for global warming which negatively impacts the environment.

Also important is the control of animal emissions of nitrogen containing compounds. Excreted compounds containing nitrogen can liberate ammonia into the environment, and this can be a major environmental concern where large numbers of livestock are congregated (e.g. feed lots and dairy operations). Increased consumption of nitrogen in certain livestock diets to maintain animal and rumen health can lead to undesirable levels of ammonia released into the environment.

An increase in propionate concentration is significant since propionate makes-up about 50% of the carbon source used by animals for growth. Butyrate is an intermediate toward the production of methane. Reduction of butyrate means a reduction in methane. The reduction in methane provides the added benefit of helping the environment by reducing greenhouse gas emissions. Overall, hop acids significantly enhance the carbon source build-up via propionate and increased energy uptake by the animal by reducing butyrate production.

Gram-negative bacteria are generally considered beneficial since they contribute to the break-down of cellulose into compounds beneficial for animal growth and energy. Gram-positive bacteria and protozoa are generally not beneficial since their digestive byproducts are not beneficial to the animal. The Gram-positive organisms that need to be controlled include *Ruminococcus albus*, *R. flavefaciens* and *Butyrivibrio fibrisolvens*. Controlling these micro-organisms has the beneficial effect of decreasing fermentation thus allowing more energy nutrients to go to the animal. Controlling the bacterium *Methanobacterium ruminatium* reduces the conversion of $H_2$ to methane gas. Controlling the various species of Streptococci and Lactobacilli also reduce the undesirable use of $H_2$ and allows more to be used in the desirable formation of propionate. Propionate is largely responsible for animal growth. *Isotricha* and Entodini are two protozoa which commonly infect the rumen. Again they take away energy and nutrients from the farm animal. During the fermentation, "good" and "bad" bacteria were allowed to compete for starch and fiber within these two feeds. Fermentations with low levels of alpha acids, beta acid, isoalpha acids, rho-isoalpha acids, tetrahydro-isoalpha acids and hexahydro-isoalpha acids are tested as well as a control that contained no hop acids. After rumenal fermentation was completed, end products were assayed to determine the effects of these hop acids.

Encapsulated Formulations

The hop acids and salts thereof used in the methods of the invention may be preserved or treated in order to minimize degradation and/or oxidation. Methods of preservation or treatment of hop acids include, but are not limited to, encapsulation, compaction, chilsonation, pelletization, or extrusion. Such techniques, including the ones described below, allow for administration of a stable hop acid or salt thereof.

In one approach, a hop derivative is provided in an encapsulated formulation (liquid or powder). Preferably, a hop derivative in liquid or powder form is encapsulated in a coating that breaks down slowly. The coating provides for the long-term release of the hop derivative. Specific materials suitable for use in capsule materials include, but are not limited to, porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a hop derivative or other compound specified above through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries. Encapsulation methods suitable for use in apiculture are described, for example, by Rieth et al., Journal of Apiculture Research 25(2):78-84 (1986).

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of hop acids. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the hop derivative is provided in an oil-based delivery system. The oil-hop derivative mix is deposited on a solid substrate and the substrate containing the hop derivative subsequently contacts and kills the bacteria. Oil release substrates include vegetable and/or mineral oils. In one embodiment, the substrate also contains a surface active agent that renders the composition readily dispersable in water; such agents include wetting agents, emulsifying agents, dispersing agents, and the like.

Hop acids of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release.

Alternatively, hop acids of the invention may also be formulated in a solid tablet and comprise (and preferably consist essentially of) an oil, a protein/carbohydrate material (preferably vegetable based), and an active ingredient. Methods for making such compositions are known in the art and are described, for example, in U.S. Patent Publication No. 20060008492. In one embodiment the invention provides a solid tablet and comprise (and preferably consist essentially of) an oil, a protein/carbohydrate material (preferably vegetable based), and a hop acid. Tablets typically contain about 4-40% (e.g., 5%, 10%, 20%, 30%, 40%) by weight of an oil (e.g., plant oil, such as corn, sunflower, peanut, olive, grape seed, tung, turnip, soybean, cotton seed, walnut, palm, castor, earth almond, hazelnut, avocado, sesame, *croton tiglium*, cacao, linseed, rape-seed, and canola oils and their hydrogenated derivatives; petroleum derived oils (e.g., paraffins and petroleum jelly), and other water immiscible hydrocarbons (e.g., paraffins). The tablets further contain from about 5-40% (e.g., 5%, 10%, 20%, 30%, 40%) by weight of a vegetable-based protein/carbohydrate material. The material contains both a carbohydrate portion (e.g., derived from cereal grains such as wheat, rye, barley, oat, corn, rice, millet, sorghum, birdseed, buckwheat, alfalfa, and mielga, corn meal, soybean meal, grain flour, wheat middlings, wheat bran, corn gluten meal, algae meal, dried yeast, beans, rice) and a protein portion. While the relative fraction of each portion making up the material may vary, the material should include at least a portion of carbohydrate and protein.

Optionally, the tablets also contain between about 10-75% (10, 15, 20, 25, 50, 75%) by weight of a sweetener. As used herein, the term "sweetener" generally refers to both natural and artificial sweeteners. Preferably, the sweetener is a sugar such as glucose, fructose, sucrose, galactose, lactose, and reversed sugar. The sugar is preferably selected from the group consisting of granulated sugar (white sugar), brown sugar, confectioner's sugar, impalpable sugar, icing sugar, and combinations thereof. Alcohols such as glycerin and complex carbohydrates, such as starches may also be used as the "sweetener" ingredient. The sweetener helps to impart a granular structure to the tablets, especially when the sweetener is a sugar. As previously discussed, this granular structure permits the tablet to crumble over time upon the exertion of sufficient forces.

Optionally, various excipients and binders can be used in order to assist with delivery of the active ingredient or to provide the appropriate structure to the tablet. Preferred excipients and binders include anhydrous lactose, microcrystalline cellulose, corn starch, magnesium estearate, calcium estearate, zinc estearate, sodic carboxymethylcellulose, ethyl cellulose, hydroxypropyl methyl cellulose, and mixtures thereof.

Tablets according to the present invention are manufactured by mixing all of the ingredients together and then compressing the mixture into a tablet of desired shape and size for a particular application. Preferably, the tablet is discoid in shape with a diameter of between about 2-5 inches and a thickness of from about 0.5-2 inches. The pressing may be accomplished by a manual or automatic pressing device. The pressure exerted on the mixture should be sufficient so as to form the tablet into a self-sustaining body.

In other embodiments, the hop acids are prepared in a dusting composition. Dusting compositions are typically prepared by grinding sugar to a fine powder and mixing into the hops acids.

Alternatively, the hop acids are prepared in a liquid spray composition that is formed by dispersing hops acids in any suitable liquid. Preferably, the hops acids are dispersed in water. If desired, the spray composition also includes a surfactant that allows the spray to be dispersed efficiently without clogging the spraying apparatus. The composition can be used to spray the animal feed.

In another approach, the hop acids of the invention are delivered in the form of a vapor.

The invention provides compositions and methods featuring a water soluble xanthohumol/cyclodextrin complex having increased stability relative to xanthohumol alone or hop acid in the absence of a delivery complex.

In one aspect, the invention generally features a composition comprising a xanthohumol (e.g., 3'-[3,3-dimethyl allyl]-2',4',4-trihydroxy-6'-methoxychalcone, a prenylated chalcone derived from hops, xanthoangelol, xanthoangelol F, 4-hydroxyderricin, 4-O-methylxanthohumol, isobavachalcone, xanthoangelol H, xanthogalenol, desmethoxyxanthohumol, 5'-prenylxanthohumol, tetrahydroxanthohumol, 2',4',6',4-terahydroxy-3'-C-geranylchalcone, dehydrocycloxanthohumol, 4-O-5'-C-diphenylxanthohumol, 4'-O-methylxanthohumol, and a xanthohumol metabolite or derivative), and a cyclodextrin (e.g., alpha-cyclodextrin, beta-cyclodextrin, gamma-cyclodextrin, hydroxypropyl-beta-cyclodextrin, sulfobutyl ether-beta-cyclodextrin, heptakis(2,6-di-O-methyl)-beta cyclodextrin, $C_{1-24}$-alkyl-gamma-cyclodextrin, and $C_{1-24}$-hydroxyalkyl-gamma-cyclodextrin), wherein the xanthohumol and the cyclodextrin form a complex.

In another aspect, the invention provides a method of preparing a xanthohumol/cyclodextrin complex, comprising combining xanthohumol and cyclodextrin and adjusting the pH to 10-12, thereby providing for xanthohumol/cyclodextrin complex formation. In one embodiment, the method further involves recovering the complex (e.g., by re-adjusting the pH to 6-9 to allow precipitation of the xanthohumol/cyclodextrin complex). In yet another embodiment, the xanthohumol and cyclodextrin are present in water or a water-miscible solvent that is any one or more of methanol, ethanol, propanol, isopropanol, glycerine, ethylene, glycol, and polyethylene glycol (PEG). In one embodiment, the water-miscible solvent is ethanol. In yet another embodiment, cyclodextrin selectively forms a complex with xanthohumol. In yet another embodiment, cyclodextrin fails to form a complex with isoxanthohumol or forms only a negligible amount (e.g., less than about 10%, 7%, 5%, 3%, 2%, 1%, 0.5% of the composition by weight) of a cyclolextrin/isoxanthohumol complex.

In another aspect, the invention provides a composition comprising a xanthohumol/cyclodextrin complex obtained by the method of a previous aspect or any method delineated herein. Xanthohumol (3'-[3,3-dimethyl allyl]-2',4',4-trihydroxy-6'-methoxychalcone) is a prenylated chalcone derived from hops (*Humulus lupulus* L.), specifically the female flowers of the hop plant, which are used in the brewing industry to add flavor and bitterness to beer. Xanthohumol isomerizes to form isoxanthohumol, particularly when compositions containing xanthohumol are heated or stored. As reported herein, to reduce susceptibility to isomerization, xanthohumol may be complexed with cyclodextrin.

The enzymatic degradation of starch by cyclodextrin-glycosyltransferase (CGT) produces cyclic oligomers, termed cyclodextrins. Cyclodextrins are non-reducing, crystalline, water soluble, cyclic oligosaccharides that consist of glucose monomers arranged in a toroidal shape, which forms a tight conical cylinder having a hydrophilic exterior (due to the presence of hydroxyl radicals) and a hydrophobic interior cavity. The hydrophobic internal cavity provides for the formation of inclusion complexes with a variety of "guest" hydrophobic molecules (e.g. aromatics, alcohols, halides, fatty acids, esters). Naturally occurring cyclodextrins include α (6 sugar units), β (7 sugar units) and γ (8 sugar units) cyclodextrins.

Cyclodextrins can be modified by various procedures, such as substituting one or more hydrogen atoms in the primary and/or secondary hydroxyl groups. Chemically modified cyclodextrins exhibit substantially increased aqueous solubility while retaining the ability to form inclusion complexes. Cyclodextrin inclusion is a molecular phenomenon in which at least one guest molecule interacts with the cavity of a cyclodextrin molecule to form a stable association. Depending on the molecular weight of the guest, more than one guest molecule may fit into the cavity. Likewise, high molecular weight molecules may bind more than one Cyclodextrin molecule. Therefore a 1 to 1 molar ratio between the guest and the cyclodextrin may not be achieved. Cyclodextrins form inclusion complexes with a broad range hydrophobic molecules. Complex formation may enhance the aqueous solubility of poorly soluble compounds and enhance the stability of agents susceptible to deterioration.

Xanthohumol/cyclodextrin complexes can be prepared as described herein. Briefly, a hop acid, or salt thereof, comprising xanthohumol is mixed with a cyclodextrin and water or a water miscible solvent to form a mixture. The pH of the mixture is adjusted to 10-12 providing for complex formation between the cyclodextrin and the xanthohumol. The complex is recovered using any method known in the art, such as by collecting the mixture containing the complex or spray-drying the mixture to obtain a complex-containing powder. In one embodiment, insoluble materials are removed, and the mixture containing the complex is acidified to reach a pH value of 6-9, providing for complex precipitation. The mixture is then maintained at a suitable temperature (e.g., room temperature) for a sufficient period of time (e.g., 2 hr, 6 hr, or 12 hr) to provide for optimal precipitation. The precipitated complex is then collected by any means known in the art, such as centrifugation or filtration. If desired, the precipate is washed with suitable solvents and dried.

In the method described above, when spent hops are used as the substance containing a xanthohumol compound, they are dispersed in water together with a cyclodextrin compound to form a mixture. The water-insoluble materials present in the spent hops are removed by any means known in the art, such as filtration or centrifugation. This step may be carried out before or after the pH is adjusted to 10-12. When a xanthohumol compound and a cyclodextrin compound are used as the starting materials in the aforementioned method, they are dissolved together in water or a water miscible solvent to form a solution. Alternatively, the xanthohumol compound is dissolved in water or a water miscible solvent first and then mixed with an aqueous solution containing the cyclodextrin compound to form a solution. The solution is then adjusted to pH 10-12. Xanthohumol/cyclodextrin compounds are then precipitated as described above.

As described herein, cyclodextrin selectively forms a complex with xanthohumol, but fails to form a complex with isoxanthohumol or forms a reduced level of such complexes. For example, a composition of the invention comprises less than about 10%, 7%, 5%, 3%, 1%, 0.5% cyclodextrin/isoxanthohumol complexes.

Without being bound by theory, a xanthohumol-containing composition is likely to be useful an antioxidant. Xanthohumol is a well-known antioxidant. See e.g., Stevens et al., Chem. Res. Toxicol., 16(10):1277-1286 (2003).

Accordingly, the present invention provides methods of preventing oxidation and/or degradation of a hop acid which comprise administering an effective amount of a pharmaceutical composition comprising a hop acid to a ruminant animal.

Methods of delivering an active ingredient to an animal feed according to the present invention comprise spray drying, encapsulation, chilsonation, compaction, pelletizing, extruding, and other methods known to those of ordinary skill in the art.

EXAMPLES

Example 1

Analysis of Ruminal Samples from Cattle Fed Hop Beta Acids

Background: Cattle were fed concentrate-based diets and were administered beta acids of hops (0, 10, 80, 160, 240, or 300 mg/day) or Rumensin (300 mg/day) to determine effects of the additives on ruminal microbiota. Rumen samples were periodically taken and pH, acetate, propionate, butyrate isobutyrate, valerate isovalerate, and total volatile fatty acid (VFA) concentrations were measured.

Materials and Methods: A 10% beta acids solution (standard aqueous alkaline solution of beta acids) was subjected to dilution. Dilutions of the 10% beta acids solution were prepared (with water and KOH additions) such that solutions were prepared that contained the proper amount of beta acids (per ml) to provide proper cattle dose in 30 ml total volume (e.g. a solution was prepared that had 10 mg/30 ml (pH of 10.5) and was used to treat the 10 mg/steer/day group; another solution was prepared that had 80 mg/30 ml (pH 10.5) and was used to treat the 80 mg/steer/day group). Each animal was treated with it appropriate 30 ml of solution, once per day.

A subset of ruminal fluid samples representing each of the seven treatment groups (control, five levels of beta acids and Rumensin). The beta acid levels were 10, 80 and 160, 240 and 300 mg/animal daily. The rumen fluid sampling was performed at prescribed intervals following feeding. Rumen samples were analyzed using standard accepted methodologies, and concentrations of parameters of interest determined.

Results: Described in Tables I through XI are the averaged results from the 24 hour feeding period (i.e. average of analysis results for each parameter, complied from samples taken and analyzed over the course of the 24 hour feeding period) for: the control animals, the animals receiving beta acids treatments (average value at all five levels), and Rumensin treated animals. The Tables provide the maximum, minimum and average values observed. The beta acids (β-acids) and Rumensin values are reported as a percentage of the control. Positive percentage values mean that the treatment (beta acids or Rumensin) exceeded the control by the specified amount (negative values less than control by specified amount.

Table I displays the results for rumen pH value.

TABLE I

Ruminal pH 24 hrs of Feeding Data

|  | Control pH | β-acids % differ from Control | Rumensin % differ from Control |
|---|---|---|---|
| Max | 6.60 | −4.24% | −5.45% |
| Min | 5.18 | 0.39% | −2.70% |
| Ave | 5.69 | −1.71% | −4.45% |

Table II displays the results for rumen ammonia concentration.

TABLE II

Ruminal Ammonia Concentration (mM)

24 hrs of Feeding Data

|  | Control Ammonia | β-acids % differ from Control | Rumensin % differ from Control |
|---|---|---|---|
| Max | 7.2 | 11.1% | −41.7% |
| Min | 0.7 | 228.6% | −54.3% |
| Ave | 3.4 | 31.8% | −54.1% |

Table III displays the results for rumen acetate concentration.

TABLE III

Acetate Concentration (mM)

24 hrs of Feeding Data

|  | Control Acetate | β-acids % differ from Control | Rumensin % differ from Control |
|---|---|---|---|
| Max | 49 | 2% | −2% |
| Min | 28 | 21% | 11% |
| Ave | 38 | 11% | 9% |

Table IV displays the results for rumen propionate concentration.

TABLE IV

Propionate Concentration (mM)

24 hrs of Feeding Data

|  | Control Propionate | β-acids % differ from Control | Rumensin % differ from Control |
|---|---|---|---|
| Max | 40 | 2.5% | 12.5% |
| Min | 18 | 27.8% | 22.2% |
| Ave | 29 | 16.1% | 27.9% |

Table V displays the results for rumen acetate:propionate ratio.

TABLE V

Ruminal Acetate:Propionate Ratio 24 hrs of Feeding Data

|  | Control A:P ratio | β-acids % differ from Control | Rumensin % differ from Control |
|---|---|---|---|
| Max | 1.73 | 9.8% | 4.0% |
| Min | 1.30 | 2.3% | −25.4% |
| Ave | 1.50 | 4.6% | −20.4% |

Table VI displays the results for rumen butyrate concentration.

TABLE VI

Butyrate Concentration (mM)

24 hrs of Feeding Data

|  | Control Butyrate | β-acids % differ from Control | Rumensin % differ from Control |
|---|---|---|---|
| Max | 12.6 | −7.1% | −8.7% |
| Min | 6.6 | 19.7% | −75.8% |
| Ave | 9.3 | 8.9% | 0.6% |

Table VII displays the results for rumen isobutyrate concentration.

TABLE VII

Isobutyrate Concentration (mM)

24 hrs of Feeding Data

|  | Control Isobutyrate | β-acids % differ from Control | Rumensin % differ from Control |
|---|---|---|---|
| Max | 1.00 | 14.00% | 5.00% |
| Min | 0.57 | 28.07% | 17.54% |
| Ave | 0.79 | 16.23% | 6.84% |

Table VIII displays the results for rumen valerate concentration.

TABLE VIII

Valerate Concentration (mM)

24 hrs of Feeding Data

|  | Control Valerate | β-acids % differ from Control | Rumensin % differ from Control |
|---|---|---|---|
| Max | 3.80 | 0.0% | 39.5% |
| Min | 1.9 | 36.8% | 36.8% |
| Ave | 3.06 | 8.0% | 31.7% |

Table IX displays the results for rumen isovalerate concentration.

TABLE IX

Isovalerate Concentration (mM)

24 hrs of Feeding Data

|  | Control Isovalerate | β-acids % differ from Control | Rumensin % differ from Control |
|---|---|---|---|
| Max | 1.81 | 26.0% | 26.0% |
| Min | 0.88 | 77.3% | 50.0% |
| Ave | 1.25 | 46.0% | 33.4% |

Table X displays the results for rumen total VFA concentration.

TABLE X

Total VFA Concentration (mM)

24 hrs of Feeding Data

|  | Control Total VFA | β-acids % differ from Control | Rumensin % differ from Control |
|---|---|---|---|
| Max | 107 | 0.9% | 0.9% |
| Min | 57 | 21.1% | 14.0% |
| Ave | 82 | 11.7% | 14.9% |

Table XI displays the results for rumen lactate concentration.

TABLE XI

Lactate Concentration (mM)

24 hrs of Feeding Data

|  | Control Lactate | β-acids % differ from Control | Rumensin % differ from Control |
|---|---|---|---|
| Max | 3.0 | −26.7% | 66.7% |
| Min | 0.2 | 0.0% | 0.0% |
| Ave | 0.6 | −30.1% | 10.2% |

It was observed from Table I that the beta acids treatment of the animals had a lower average rumen pH when compared to the control animals (−1.71% lower than control), but that the pH was closer to the control than the Rumensin treated animals (Rumensin average pH=−4.45% of control). The pH of the rumen is very important for rumen and animal health. It was surprising and unexpected to find that the beta acids treated animals had a higher rumen pH than the Rumensin treated animals as it was assumed that the rumen pH effect of beta acids and rumensin would be comparable due to there assumed similar impact on rumen microflora (e.g. inhibition of Gram-positive organisms). The slightly higher pH of the rumen in beta acid treated animals was significant as pH is a log scale and a small change in pH towards neutrality has a significant effect on the microbial population and promotion of rumen enzymatic action.

The rumen pH findings were supported by the rumen ammonia concentration findings. In Table II it was observed that rumen ammonia was higher for the beta acids treated animals. The rumen ammonia may contribute to a "buffering effect" on the rumen, and it may have been this buffering effect that helped the beta acids treated animals achieve a higher rumen pH than the Rumensin treated animals.

In Tables III through X are the data for the acetate, propionate, acetate:propionate, butyrate, isobutyrate, valerate, isovalerate, and volatile fatty acid. In all cases, the beta acids treated animals (on average) exceeded the control animals for fatty acid concentrations. The beta acid treated animals had fatty acid profiles indicative of excellent rumen performance.

Table XI contained the rumen lactate concentration data, and as would be expected from a treatment that would control lactic acid (Gram-positive) organisms, the beta acids treated animals had low lactate levels.

All references cited herein, whether in print, electronic, computer readable storage media or other form, are expressly incorporated by reference in their entirety, including but not limited to, abstracts, articles, journals, publications, texts, treatises, technical data sheets, interne web sites, databases, patents, patent applications, and patent publications.

The discussion above is descriptive, illustrative and exemplary and is not to be taken as limiting the scope defined by any appended claims.

What is claimed is:

1. A method for improving rumen health and functionality of a group of ruminant animals comprising the oral administration of a rumen pH modulating amount of a hop acid to the ruminant animals;
   wherein the rumen health and functionality are relative to a group of ruminant animals that is fed an animal feed that is free of a rumen pH modulating amount of a hop acid.

2. The method of claim 1, wherein the oral administration of hop acids in a ruminant's diet includes a feed composition, feed supplement, feed ration, water ration, mineral lick, and/or bolus.

3. The method of claim 1, wherein the hop acid is derived from a hop or hop source, or is produced synthetically.

4. The method of claim 3, wherein the hop acid is a hop β-acid.

5. The method of claim 4, wherein the hop β-acid is lupulone, colupulone, adlupulone, hexahydro-lupulone, hexahydro-colupulone, hexahydro-adlupulone, or hulupone.

6. The method of claim 3, wherein the hop acid is a hop α-acid.

7. The method of claim 6, wherein the hop α-acid is humulone, cohumulone, adhumulone, isohumulone, isocohumulone, isoadhumulone, dihydro-isohumulone, dihydro isocohumulone, dihydro-isoadhumulone, tetrahydro-isohumulone, tetrahydro-isocohumulone, tetrahydro-isoadhumulone, hexahydro-isohumulone, hexahydro-isocohumulone, or hexahydro-isoadhumulone.

8. The method of claim 1, wherein the amount of hop acid administered to the ruminant animal is between 0.1-1000 mg/animal/day.

9. The method of claim 8, wherein the hop acid is administered in an effective amount, including but not limited to, as part of a formulation, compounded mixture, salt, hydrate, solvate, and/or polymorph.

10. The method of claim 1, wherein the pH of a rumen fluid or intestinal digesta sample from the time immediately upon initiation of feeding to 24 hours post-feeding is maintained in a range from about 5 to 8.

11. The method of claim 1, wherein the pH of rumen fluid or intestinal digesta sample from the time immediately upon initiation of feeding to 24 hours post-feeding is maintained in the preferable range from about 5.2 to 7.

12. The method of claim 1, wherein the animal does not suffer from acidosis.

13. The method of claim 1, wherein the pH of the animal rumen is higher than the pH of an animal rumen that is administered an animal feed treated with a polyether ionophore compound in the absence of hop acids.

14. The method of claim 1, wherein rumen ammonia production is increased in the ruminant animal compared to a ruminant animal not administered hop acid.

* * * * *